(12) United States Patent
Pletcher et al.

(10) Patent No.: US 8,857,981 B2
(45) Date of Patent: Oct. 14, 2014

(54) FACILITATION OF CONTACT LENSES WITH CAPACITIVE SENSORS

(75) Inventors: Nathan Pletcher, Mountain View, CA (US); Brian Otis, Sunnyvale, CA (US)

(73) Assignee: Google Inc., Mountain View, CA (US)

(*) Notice: Subject to any disclaimer, the term of this patent is extended or adjusted under 35 U.S.C. 154(b) by 83 days.

(21) Appl. No.: 13/559,384

(22) Filed: Jul. 26, 2012

(65) Prior Publication Data
US 2014/0192312 A1 Jul. 10, 2014

(51) Int. Cl.
G02C 1/00 (2006.01)
G02C 11/00 (2006.01)
G02C 7/04 (2006.01)

(52) U.S. Cl.
CPC .............. G02C 11/10 (2013.01); G02C 7/049 (2013.01)
USPC ..................................... 351/158; 351/159.02

(58) Field of Classification Search
CPC ......... G02C 11/00; G02C 11/10; G02C 7/049
USPC ................................ 351/158, 159.01, 159.02
See application file for complete search history.

(56) References Cited

U.S. PATENT DOCUMENTS

| | | | |
|---|---|---|---|
| 3,958,560 A | 5/1976 | March | |
| 4,014,321 A | 3/1977 | March | |
| 4,055,378 A | 10/1977 | Feneberg et al. | |
| 4,122,942 A | 10/1978 | Wolfson | |
| 4,136,250 A | 1/1979 | Mueller et al. | |
| 4,143,949 A | 3/1979 | Chen | |
| 4,153,641 A | 5/1979 | Deichert et al. | |
| 4,214,014 A | 7/1980 | Hofer et al. | |
| 4,309,085 A | 1/1982 | Morrison | |
| 4,312,575 A | 1/1982 | Peyman et al. | |

(Continued)

FOREIGN PATENT DOCUMENTS

| EP | 0369942 | 5/1990 |
|---|---|---|
| EP | 686372 | 12/1995 |

(Continued)

OTHER PUBLICATIONS

Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.

(Continued)

*Primary Examiner* — Huy K Mai
(74) *Attorney, Agent, or Firm* — McDonnell Boehnen Hulbert & Berghoff LLP

(57) ABSTRACT

Apparatus, systems and methods employing contact lens with capacitive sensors are provided. In some aspects, a contact lens includes: a substrate; a capacitive sensor, disposed on or within the substrate, that senses a capacitance on the contact lens; and a circuit disposed on or within the substrate. In some aspects, the circuit can include a capacitance analysis component that determines a condition of an eyelid associated with the eye over which the contact lens is disposed and/or a parameter associated with the eye over which the contact lens is disposed. In some aspects, the condition can be a blink of an eyelid. In some aspects, the parameter can be at least one of a pressure of an object in proximity to the contact lens, a thickness or type of a layer of material disposed on or within the contact lens or a composition of material on the contact lens.

14 Claims, 12 Drawing Sheets

(56) References Cited

U.S. PATENT DOCUMENTS

| | | |
|---|---|---|
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint et al. |
| 5,177,165 A | 1/1993 | Valint, Jr. et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicholson et al. |
| 5,908,906 A | 6/1999 | Kunzler et al. |
| 5,981,669 A | 11/1999 | Valint et al. |
| 6,087,941 A | 7/2000 | Ferraz |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 8,348,422 B2 * | 1/2013 | Pugh et al. ............... 351/159.02 |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0221276 A1 | 10/2005 | Rozakis et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |
| 2012/0075168 A1 | 3/2012 | Osterhout et al. |
| 2012/0075574 A1 | 3/2012 | Pugh et al. |
| 2012/0078071 A1 | 3/2012 | Bohm et al. |
| 2012/0088258 A1 | 4/2012 | Bishop et al. |
| 2012/0092612 A1 | 4/2012 | Binder |
| 2012/0109296 A1 | 5/2012 | Fan |
| 2012/0177576 A1 | 7/2012 | Hu |

(56) References Cited

U.S. PATENT DOCUMENTS

| | | |
|---|---|---|
| 2012/0201755 A1 | 8/2012 | Rozakis et al. |
| 2012/0245444 A1 | 9/2012 | Otis et al. |
| 2012/0259188 A1 | 10/2012 | Besling |

FOREIGN PATENT DOCUMENTS

| | | |
|---|---|---|
| EP | 1061874 | 12/2000 |
| EP | 1617757 | 1/2006 |
| EP | 1818008 | 8/2007 |
| EP | 1947501 | 7/2008 |
| EP | 2457122 | 5/2012 |
| WO | 95/04609 | 2/1995 |
| WO | 0116641 | 3/2001 |
| WO | 01/34312 | 5/2001 |
| WO | 03065876 | 8/2003 |
| WO | 2004/060431 | 7/2004 |
| WO | 2004064629 | 8/2004 |
| WO | 2006015315 | 2/2006 |
| WO | 2009094643 | 7/2009 |
| WO | 2010105728 | 9/2010 |
| WO | 2010/133317 | 11/2010 |
| WO | 2011/011344 | 1/2011 |
| WO | 2011034592 | 3/2011 |
| WO | 2011035228 | 3/2011 |
| WO | 2011035262 | 3/2011 |
| WO | 2011083105 | 7/2011 |
| WO | 2011163080 | 12/2011 |
| WO | 2012035429 | 3/2012 |
| WO | 2012037455 | 3/2012 |
| WO | 2012051167 | 4/2012 |
| WO | 2012051223 | 4/2012 |
| WO | 2012052765 | 4/2012 |

OTHER PUBLICATIONS

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.
Bionic contact lens 'to project emails before eyes,' http://www.kurzweilai.net/forums/topic/bionic-contact-lens-to-project-emails-before-eyes, Last accessed Mar. 14, 2012, 2 pages.
Tweedie, et al., "Contact creep compliance of viscoelastic materials via nanoindentation," J. Mater. Res., Jun. 2006, vol. 21, No. 2, pp. 1576-1589, Materials Research Society.
Brahim, et al., "Polypyrrole-hydrogel composites for the construction of clinically important biosensors," 2002, Biosensors & Bioelectronics, vol. 17, pp. 53-59.
Huang, et al., "Wrinkling of Ultrathin Polymer Films," Mater. Res. Soc. Symp. Proc., 2006, vol. 924, 6 pages, Materials Research Society.
Zarbin, et al., "Nanotechnology in ophthalmology," Can J Ophthalmol, 2010, vol. 45, No. 5, pp. 457-476.
Selner, et al., "Novel Contact Lens Electrode Array for Multi-electrode Electroretinography (meERG)," IEEE, 2011, 2 pages.
Liao, et al., "A 3-µW CMOS Glucose Sensor for Wireless Contact-Lens Tear Glucose Monitoring," IEEE Journal of Solid-State Circuits, Jan. 2012, vol. 47, No. 1, pp. 335-344.
Chen, et al. "Microfabricated Implantable Parylene-Based Wireless Passive Intraocular Pressure Sensors," Journal of Microelectromechanical Systems, Dec. 2008, vol. 17, No. 6, pp. 1342-1351.
Thomas, et al., "Functional Contact Lenses for Remote Health Monitoring in Developing Countries," IEEE Global Humanitarian Technology Conference, 2011, pp. 212-217, IEEE Computer Society.
Pandey, et al., "A Fully Integrated RF-Powered Contact Lens With a Single Element Display," IEEE Transactions on Biomedical Circuits and Systems, Dec. 2010, vol. 4, No. 6, pages.
Lingley, et al., "Multipurpose integrated active contact lenses," SPIE, 2009, 2 pages.

Chu, et al., "Soft Contact-lens Sensor for Monitoring Tear Sugar as Novel Wearable Device of Body Sensor Network," http://www.ksi.edu/seke/dms11/DMS/2_Kohji_Mitsubayashi.pdf, Last accessed Jul. 27, 2012, 4 pages.
Liao, et al., "A 3µW Wirelessly Powered CMOS Glucose Sensor for an Active Contact Lens," 2011 IEEE International Solid-State Circuits Conference, Session 2, Feb. 21, 2011, 3 pages.
Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.
Lončar, et al., "Design and Fabrication of Silicon Photonic Crystal Optical Waveguides," Journal of Lightwave Technology, Oct. 2000, vol. 18, No. 10, pp. 1402-1411.
Liu, et al., "Miniature Amperometric Self-Powered Continuous Glucose Sensor with Linear Response," Analytical Chemistry, 7 pages.
Baxter, "Capacitive Sensors," 2000, 17 pages.
Lingley, et al., "A Single-Pixel Wireless Contact Lens Display," Journal of Micromechanics and Microengineering, 2011, 9 pages.
Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.
Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.
Chu et al., "Biomedical soft contact-lens sensor for in situ ocular biomonitoring of tear contents," Biomed Microdevices, 2011, pp. 603-611, vol. 13.
Chu et al., "Soft contact lens biosensor for in situ monitoring of tear glucose as non-invasive blood sugar assessment," Talanta, 2011, pp. 960-965, vol. 83.
"Contact Lenses: Look Into My Eyes," The Economist, Jun. 2, 2011, http://www.economist.com/node/18750624/print, Last accessed Mar. 13, 2012, 8 pages.
Haders, "New Controlled Release Technologies Broaden Opportunities for Ophthalmic Therapies," Drug Delivery Technology, Jul./Aug. 2009, pp. 48-53, vol. 8, No. 7.
Ho et al., "Contact Lens With Integrated Inorganic Semiconductor Devices," MEMS 2008. IEEE 21st International Conference on. IEEE, 2008., pp. 403-406.
Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012. 5 pages.
Lähdesmäki et al., "Possibilities for Continuous Glucose Monitoring by a Functional Contact Lens," IEEE Instrumentation & Measurement Magazine, Jun. 2010, pp. 14-17.
Lingley et al., "A contact lens with integrated micro solar cells," Microsyst Technol, 2012, pp. 453-458, vol. 18.
Murdan, "Electro-responsive drug delivery from hydrogels," Journal of Controlled Release, 2003, pp. 1-17, vol. 92.
Parviz, Babak A., "For Your Eyes Only," IEEE Spectrum, Sep. 2009, pp. 36-41.
Saeedi, E. et al., "Self-assembled crystalline semiconductor optoelectronics on glass and plastic," J. Micromech. Microeng., 2008, pp. 1-7, vol. 18.
Saeedi et al., "Self-Assembled Inorganic Micro-Display on Plastic," Micro Electro Mechanical Systems, 2007. MEMS. IEEE 20th International Conference on. IEEE, 2007., pp. 755-758.
Sensimed Triggerfish, Sensimed Brochure, 2010, 10 pages.
Shih, Yi-Chun et al., "An Inductorless DC-DC Converter for Energy Harvesting With a 1.2-µW Bandgap-Referenced Output Controller," IEEE Transactions on Circuits and Systems-II: Express Briefs, Dec. 2011, pp. 832-836, vol. 58, No. 12.
Shum et al., "Functional modular contact lens," Proc. of SPIE, 2009, pp. 73970K-1 to 73970K-8, vol. 7397.
Singh, et al., "Novel Approaches in Formulation and Drug Delivery using Contact Lenses," Journal of Basic and Clinical Pharmacy, May 2011, pp. 87-101, vol. 2, Issue 2.
Stauth et al., "Self-assembled single-crystal silicon circuits on plastic," PNAS, Sep. 19, 2006, pp. 13922-13927, vol. 103, No. 38.

(56) References Cited

OTHER PUBLICATIONS

Yao, H. et al., "A contact lens with integrated telecommunication circuit and sensors for wireless and continuous tear glucose monitoring," J. Micromech. Microeng., 2012, pp. 1-10, vol. 22.

Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.

Yao et al., "A contact lens with embedded sensor for monitoring tear glucose level," Biosensors and Bioelectronics, 2011, pp. 3290-3296, vol. 26.

Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.

Yeager et al., "A 9 µA, Addressable Gen2 Sensor Tag for Biosignal Acquistion," IEEE Journal of Solid-State Circuits, Oct. 2010, pp. 2198-2209, vol. 45, No. 10.

Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

\* cited by examiner

FACILITATION OF CONTACT LENSES WITH CAPACITIVE SENSORS

TECHNICAL FIELD

This disclosure generally relates to contact lenses with capacitive sensors.

BACKGROUND

Detecting conditions associated with the eye and/or materials near or on the eye can be intrusive and tedious. Methods for performing detection in a non-intrusive and efficient manner are desirable.

SUMMARY OF THE INVENTION

Figure 1:
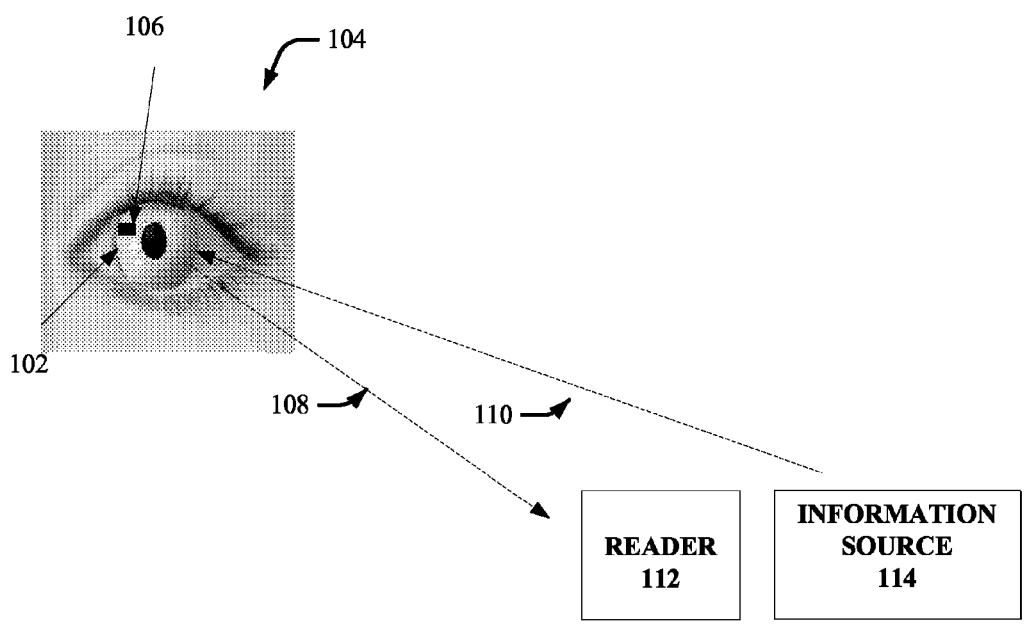
FIG. 1 is an illustration of a block diagram of an exemplary non-limiting system that facilitates capacitive sensing on a contact lens in accordance with aspects described herein.

Various aspects are now described with reference to the drawings, wherein like reference numerals are used to refer to like elements throughout. In the following description, for purposes of explanation, numerous specific details are set forth in order to provide a more thorough understanding of one or more aspects. It is be evident, however, that such aspects can be practiced without these specific details. In other instances, structures and devices are shown in block diagram form in order to facilitate describing one or more aspects.

It is to be appreciated that in accordance with one or more aspects described in this disclosure, users can opt-in or opt-out of providing personal information, demographic information, location information, proprietary information, sensitive information, or the like in connection with data gathering aspects. Moreover, one or more aspects described herein can provide for anonymizing collected, received, or transmitted data.

Capacitance is a property that exists between two conductive surfaces (e.g., metal plates) within proximity to one another. The size of the conductive plates, distance to one another and the material (e.g., dielectric) between the surfaces can all affect the capacitance. Further, a change in distance between conductive surfaces or proximity of a material or fluid near conductive surfaces can cause change of capacitance due to change in electric field associated with the conductive surfaces.

Capacitive sensing is employed to detect or measure proximity to a sensor, humidity, fluid level, touch or acceleration. Because biological materials emitted from an eye region are in proximity to a contact lens over the eye, capacitive sensors on the contact lens can change capacitance based on change in electric field when biological materials approach the contact lens. Similarly, fingers and other objects can change capacitance on a contact lens.

In proximity sensing, capacitance is inversely proportional to distance between two capacitor plates. Because the distance-capacitance relationship is asymptotic, proximity sensing works well in applications in which high resolution in close proximity is desired. Accordingly, detection of materials and/or objects (e.g., fingers) in proximity to contact lenses is an ideal function for capacitive proximity sensors.

Numerous different types of capacitance measuring circuits exist. For example, oscillation-based measuring circuits oscillate at a frequency that depends on the capacitance of a capacitive sensor. The frequency indicates capacitance of the capacitive sensor. Inductance-based and current-based measuring circuits also exist.

Apparatus, systems and methods disclosed herein relate to contact lenses having one or more capacitive sensors. The contact lens can include: a substrate; at least one capacitive sensor disposed on or within the substrate, that senses capacitance on the contact lens; and a circuit disposed on or within the substrate. In some aspects, the circuit can include a capacitance analysis component that determines condition of an eyelid associated with an eye over which the contact lens is disposed and/or a parameter associated with the eye over which the contact lens is disposed. In some aspects, the condition can be a blink of an eyelid. In some aspects, the parameter can be at least one of a pressure sensor on a contact lens, thickness of a layer of material disposed on or within the contact lens, type of material on the contact lens or composition of material on the contact lens.

One or more of the aspects can advantageously employ capacitive sensing on an eyelid to determine or infer and/or report physical conditions associated with the eye and/or eyelid in a non-intrusive and efficient manner. For example, different conditions that can be determined or inferred by detecting change in capacitance includes, but is not limited to, eyelid movement, direction of eyelid movement, blinking, frequency of blinking, change in environment, pollution level, allergen level, fluid level, presence of tears, eye pressure (e.g., associated with emotional state). As described above, the information collected, received and/or transmitted can be anonymized. Further, contact lens wearers can opt-in or opt-out of providing information in connection with data gathering.

DETAILED DESCRIPTION

FIG. 1 is an illustration of a diagram of an exemplary non-limiting system that facilitates capacitive sensing on a contact lens in accordance with aspects described herein. The system 100 can include a contact lens 102 covering at least a portion of an eye 104 of wearer of the contact lens 102. The contact lens 102 can include a substrate (not shown), and a circuit 106 and capacitive sensor (not shown) disposed on or within a substrate of the contact lens 102. In some aspects, when the components are disposed within the substrate, the components can be encapsulated within the substrate.

The capacitive sensor can determine capacitance on the contact lens 102. For example, as described in further detail with reference to FIGS. 2A, 2B, 2C and 3, the capacitive sensor can be composed of at least two electrodes that have a baseline capacitance between the electrodes. For example, the electrodes can be or include metal plates having a dielectric constant that changes as an object or material moves closer to or further from the electrodes. Accordingly, the baseline capacitance can then change as a result of an object or material in proximity to the electrodes. For example, material on or near the contact lens can cause change in the baseline capacitance between the electrodes. The change in the capacitance can be sensed and employed in determining nature and/or identity of material in proximity to the electrodes. Alternately, or additionally, the sensor can measure a physical distance between the conductive plates as measured with the capacitance sensor.

In various aspects, the electrodes can be or include any number of different types of metals or semi-metals. For example, the electrodes can be or include silicon or iron. In various aspects, the electrodes can be embedded in the substrate 202 and need not be biocompatible.

The circuit 106 of the contact lens 102 can receive sensed capacitance output from the capacitive sensor. In some aspects, the circuit 106 can include one or more components that can employ the sensed capacitance to determine condition of the eye or eyelid (e.g., a blink of the eyelid has occurred) and/or a parameter associated with the eye over which the contact lens 102 is disposed. For example, the parameter can be pressure of an object (e.g., finger, eyelid) on the contact lens, and the sensor can be a capacitive pressure sensor that changes capacitance in accordance with amount of pressure applied to the capacitive pressure sensor. In some aspects, the parameter can be related to characteristics of material on or in proximity to the contact lens. The conditions and/or parameters (or values of parameters) collected, received and/or transmitted can be anonymized. Further, contact lens wearers can opt-in or opt-out of providing information in connection with data gathering.

As another example, the parameter can be thickness of a layer of material disposed on or within the contact lens. The capacitive sensor can change baseline capacitance in accordance with amount or thickness of the material. As another example, the parameter can be type of material on the contact lens (as described above, the capacitance can change based on the type of the material). As another example, the parameter can be composition of material (the capacitance can change based on the composition of the material, which can be indicated by concentration of a certain type of substance with the material). In these aspects, the sensor can be a capacitive proximity sensor.

As described in greater detail below, in some aspects, the circuit 106 can perform operations (or cause operations to be performed) on the contact lens 102 based, at least, on sensed capacitance. Accordingly, the contact lens 102 can perform operations without input from a source external to the contact lens.

By way of example, but not limitation, the operations can include storing the sensed information and/or transferring information to a reader or a monitoring station in response to particular sensed features having particular changes in capacitance from the baseline capacitance or the like.

In some aspects, the circuit 106 can output information 108 (e.g., sensed capacitance and/or other information) to a reader 112 external to in the contact lens 102. The reader 112 can be a radio frequency (RF) reader in some aspects. The information output can include, but is not limited to, information indicative of the condition and/or parameter determined, the capacitance sensed, a frequency value or current indicative of the capacitance sensed, or the like.

In some aspects, the circuit 106 can receive information 110 from an information source 114 external to the contact lens 102. For example, the circuit 106 can receive information 110 such as actions to take on the contact lens 102 based on the sensed capacitance (or information indicative of the sensed capacitance) output from the contact lens 102. In some aspects, the actions can be computer-readable instructions that can be stored in the memory and executed by the logic circuitry on the contact lens.

Figure 2A:
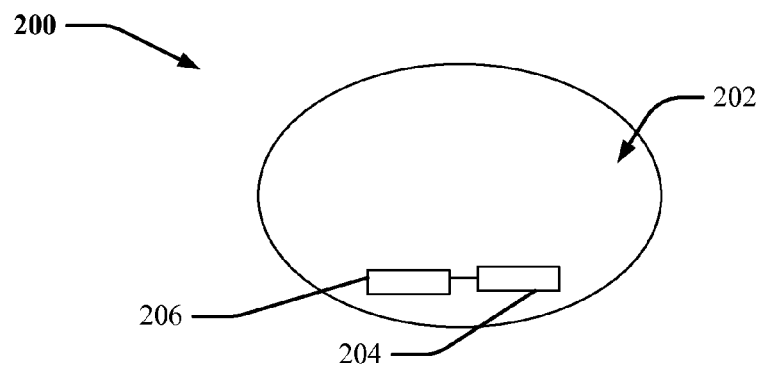
FIGS. 2A and 2B are top-view illustrations of exemplary non-limiting contact lenses with capacitive sensors in accordance with aspects described herein.
Figure 2B:
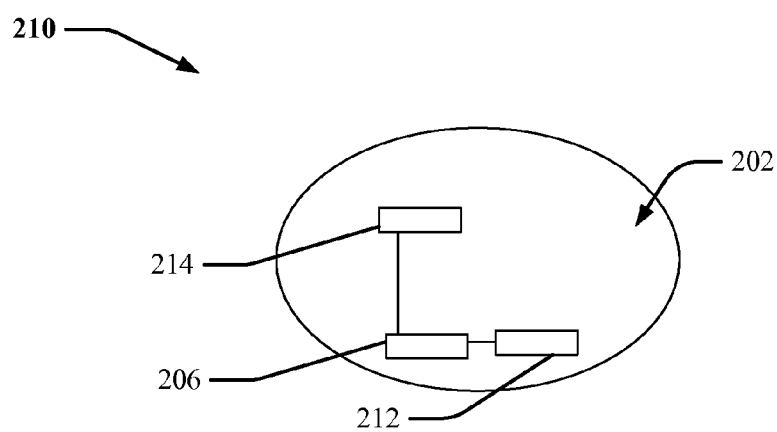

Various aspects of the contact lens 102 can include structure and/or functionality of the contact lenses described and shown with reference to FIGS. 2A, 2B and/or 2C.

FIGS. 2A and 2B are top-view illustrations of exemplary non-limiting contact lenses with capacitive sensors in accordance with aspects described herein. Turning first to FIG. 2A, the contact lens 200 includes a substrate 202 having at least one capacitive sensor 204 and a circuit 206 disposed on or within the substrate 202.

As described above, the capacitive sensor 204 can determine capacitance on the contact lens 200. In various aspects, the capacitive sensor 204 can have a baseline capacitance that changes as a result of an object in proximity to, or pressure on the contact lens. In some aspects, the baseline capacitance can change as a result of a material on or near the contact lens. The change in capacitance can be sensed in various aspects (e.g., by a capacitance proximity sensor).

As also previously described, the capacitive sensor 204 can include at least two electrodes (not shown) that have baseline capacitance between them. The capacitance between the electrodes can change in response to any number of conditions. For example, in some aspects, the electrodes can be or include metal plates having a dielectric constant that changes as an object moves closer to or further from the electrodes.

In various aspects, the electrodes can be or include any number of different types of metals or semi-metals. For example, the electrodes can be or include silicon or gold. In various aspects, the electrodes can be embedded in the substrate 202 and need not be biocompatible.

The circuit 206 can receive the sensed capacitance (or information indicative thereof). The circuit 206 can perform an action based on the sensed capacitance (e.g., store or transfer the information sensed or parameters indicative of the information sensed), communicate with an external reader or information source regarding the sensed capacitance and/or convert the sensed capacitance to frequency and/or a current as described in the subsequent paragraphs.

For example, as described with reference to FIG. 4 below, the circuit 206 can include an oscillator/frequency conversion component. The oscillator/frequency conversion component detects the sensor capacitance through a capacitance to frequency conversion. It can include a comparator having two thresholds that allow a capacitance measurement. A constant current can be used to charge/discharge the sensor capacitance. The rate of charge/discharge is proportional to the sensor capacitance. Thus, a higher output frequency is indicative of a lower sensor capacitance (and vice versa).

In lieu of or in addition to the comparator, in some aspects, the oscillator/frequency conversion component can include a Schmitt trigger circuit that would present two thresholds, also allowing a capacitance to frequency conversion. The oscillator/frequency conversion component can then oscillate at a frequency corresponding to capacitance of the capacitive sensor. Accordingly, the sensed capacitance can be converted to frequency in various aspects.

Turning now to FIG. 2B, as shown, a contact lens 210 can include a substrate 202 and at least two sensors 212, 214 and a circuit 206. Each sensor 212, 214 can be composed of two electrodes having a baseline capacitance between the two electrodes. The capacitance between each pair of electrodes of sensors 212, 214 can change in response to movement of the eyelid. For example, if the eyelid covers one of the pairs of electrodes, the capacitance for the corresponding pair of electrodes can change while the capacitance for the other, uncovered pair of electrodes can remain substantially the same. Similarly, if the eyelid covers both pairs of electrodes (e.g., if the wearer has blinked or is closing his/her eye), both of the pairs of electrodes can have a change in capacitance. Accordingly, based on which pair of electrodes have a change in capacitance, a determination can be made as to the direction that the eyelid is moving or if the eyelid has blinked or is closed.

Figure 2C:
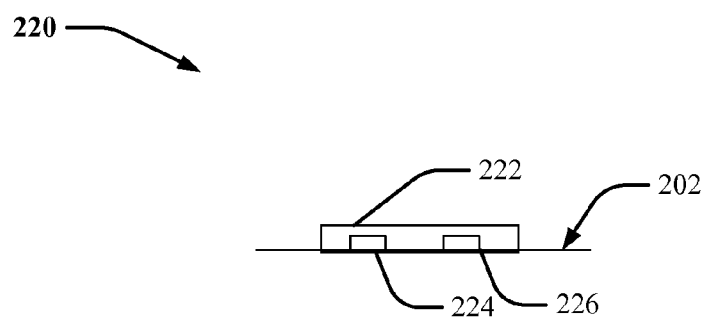
FIG. 2C is a side-view illustration of an exemplary non-limiting substrate of a contact lens with a capacitive sensor having electrodes in accordance with aspects described herein.

FIG. 2C is a side-view illustration of an exemplary non-limiting substrate of a contact lens with a capacitive sensor and electrodes in accordance with aspects described herein. As shown in FIG. 2C, in one aspect, the substrate 202 can include at least one sensor 222 having a pair of electrodes 224, 226. The electrodes 224, 226 can be disposed on or within a substantially same horizontal plane relative to one another, and can have a baseline capacitance between the electrodes 224, 226.

In other aspects, the electrodes can be on the same vertical plane. In various aspects, the plates of the electrodes can be positioned such that one of the electrodes of the pair of electrodes is closer to the bottom of the contact lens and the other electrode is closer to the top of the contact lens.

In various aspects, an eyelid, finger, and/or fluid proximate to or on the contact lens 200, or any number of other objects and/or materials, can cause a change in capacitance. In some aspects, an eyelid covering the electrodes of the capacitive sensor 204 can change capacitance in such a manner that a blink of the eyelid is determined to have occurred.

Figure 3:
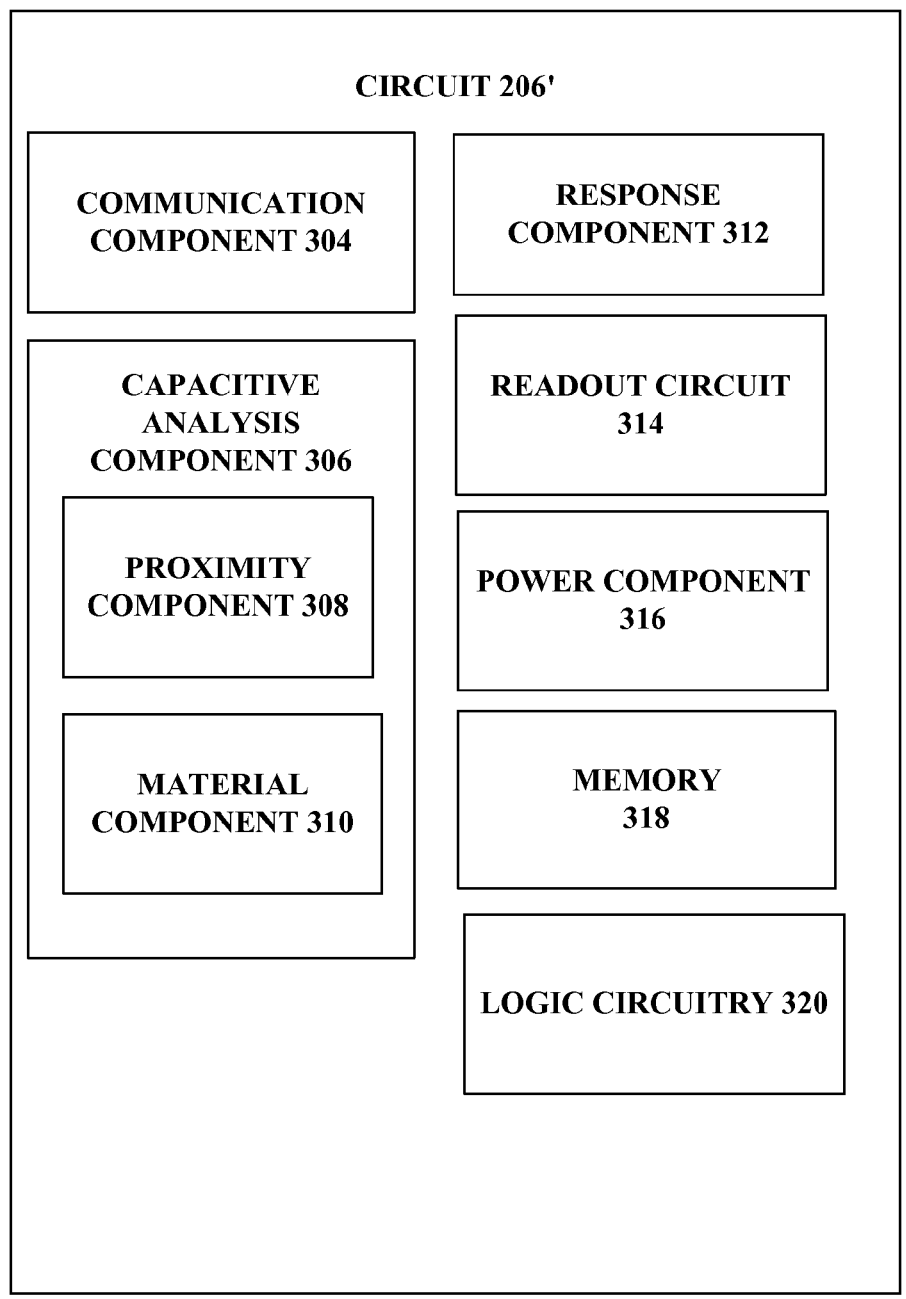
FIG. 3 is an illustration of an exemplary non-limiting diagram of a circuit for a contact lens providing capacitive sensing in accordance with aspects described herein.
Figure 4:
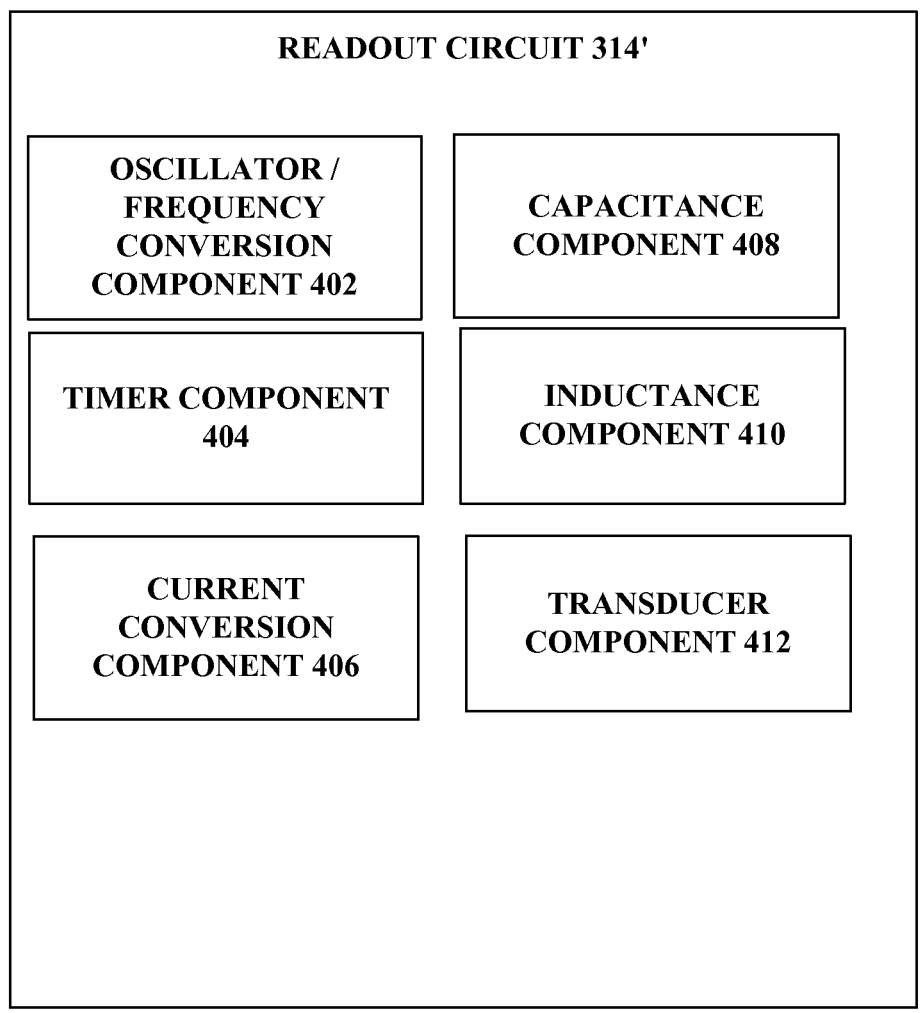
FIG. 4 is an illustration of an exemplary non-limiting diagram of a readout circuit that can be employed with a contact lens providing capacitive sensing in accordance with aspects described herein.

In various aspects, the circuit 206 can be or include one or more of the structure and/or the functionality of circuit 206' of FIG. 3 and/or readout circuit 314' of FIG. 4.

FIG. 3 is an illustration of an exemplary non-limiting diagram of a circuit for a contact lens providing capacitive sensing in accordance with aspects described herein. The circuit 206' can include a communication component 304, capacitive analysis component 306, a response component 312, a readout circuit 314, a power component 316, a memory 318 and/or logic circuitry 320. In some aspects, one or more of the communication component 304, capacitive analysis component 306, response component 312, readout circuit 314, power component 316, memory 318 and/or logic circuitry 320 can be communicatively and/or electrically coupled to one another to perform one or more functions of the circuit 206'.

The circuit can be coupled to one or more capacitive sensors disposed on or within the contact lens, and that sense capacitance on the contact lens as described with reference to FIGS. 1, 2A, 2B and/or 2C.

The communication component 304 can transmit information from and/or receive information at the circuit 206'. In various aspects, the information transmitted can be information about capacitance sensed via the capacitive sensor coupled to the circuit 206'. In various aspects, the information transmitted can be information about proximity of an object relative to the contact lens and/or a type, amount or composition of a material disposed on or within or near the contact lens. For example, the information can be about a composition of tear fluid disposed on or within the contact lens.

In some aspects, the communication component 304 can transmit the information to a reader external to the contact lens (e.g., reader 112 described with reference to FIG. 1).

In some aspects, the communication component 304 can also receive information from a location remote from the contact lens. For example, the communication component 304 can receive information from the information source 114 described with reference to FIG. 1. In some aspects, the information received can include, but is not limited to, computer-readable instructions describing actions to take on the contact lens. The actions can be in response to the sensed capacitance in some aspects.

The readout circuit 314 can detect capacitance sensed by the sensor and output information indicative of the capacitance sensed by the sensor. In various aspects, the readout circuit 314 can include the structure and/or functionality of the readout circuit 314' described below in greater detail with reference to FIG. 4.

FIG. 4 is an illustration of an exemplary non-limiting diagram of a readout circuit that can be employed with a contact lens providing capacitive sensing in accordance with aspects described herein.

The readout circuit 314' can include an oscillator/frequency conversion component 402, a timer component 404, a current conversion component 406, a capacitance component 408 and/or an inductance component 410. In various aspects, one or more of the oscillator/frequency conversion component 402, timer component 404, current conversion component 406, capacitance component 408 and/or inductance component 410 can be electrically and/or communicatively coupled to one another to perform one or more functions of the readout circuit 314'.

In some aspects, the oscillator/frequency [402] conversion component detects the sensor capacitance through a capacitance to frequency conversion. It can include a comparator having two thresholds that allow a capacitance measurement. A constant current can be used to charge/discharge the sensor capacitance. The rate of charge/discharge is proportional to the sensor capacitance. Thus, a higher output frequency is indicative of a lower sensor capacitance (and vice versa).

In some aspects, the oscillator/frequency conversion component 402 can include a Schmitt trigger circuit that would present two thresholds, also allowing a capacitance to frequency conversion.

Accordingly, the oscillator/frequency conversion component 402 can sense level of charge at the capacitive sensor. The oscillator/frequency conversion component 402 can oscillate at a frequency corresponding to capacitance of the capacitive sensor. The oscillator/frequency conversion component 402 can convert the oscillation into a frequency value in some aspects. Table 1 illustrates exemplary simulated oscillation frequencies for various sensed capacitances and Vdd=0.5 volts. The oscillation frequencies can be output from the readout circuit 314'. For example, in some aspects, the oscillation frequencies can be output to a reader (e.g., reader 112 in some aspects).

| Capacitance | Oscillation Frequency | Average Current |
|---|---|---|
| 1 femtofarad (fF) | 1.3 megahertz (MHz) | 100 nanoamperes (nA) |
| 10 fF | 1.2 MHz | 98 nA |
| 100 fF | 770 kilohertz (kHz) | 83 nA |

| Capacitance | Oscillation Frequency | Average Current |
| --- | --- | --- |
| 1 picofarad (pF) | 179 kHz | 61 nA |
| 10 pF | 34 kHz | 57 nA |
| 100 pF | 5 kHz | 56 nA |

The timer component 404 can determine amount of time for the capacitive sensor to reach a particular charge. The timer component can determine whether the capacitor has reached a full charge.

The current conversion component 406 can output a current (or information indicative of the current) from the readout circuit 314'. The output current can be a function of the capacitance sensed via the capacitive sensor.

The capacitance component 408 can output capacitance sensed via the capacitive sensor. Information indicative of the capacitance can be output from the readout circuit 314'.

The inductance component 410 can resonate with a frequency that is a function of the capacitance sensed. For example, the contact lens can include an antenna that resonates in a manner corresponding to the capacitance sensed.

The transducer component 412 can convert the information output from the oscillator/frequency conversion component 402, capacitance component 408, timer component and/or current conversion component 406 to an electrical signal that can be transmitted from the circuit 206'.

Turning back to FIG. 3, in various aspects, the capacitive analysis component 306 can detect one or more parameters and/or one or more conditions associated with the eye over which the contact lens is worn. The parameters and/or conditions can be detected based on sensed capacitance (which can be output from the readout circuit 314 in some aspects).

In some aspects, the capacitive analysis component 306 can include a proximity component 308 and/or a material component 310. Accordingly, the capacitive analysis component 306 can determine numerous different conditions and/or parameters. In some aspects, the capacitive analysis component 306 can detect presence of a particular material on the eye, a blink of an eyelid, a direction of movement of the eyelid, and/or an orientation of the contact lens, for example.

The proximity component 308 can receive the sensed capacitance. Based on the change between the baseline capacitance and the sensed capacitance, the proximity component 308 can determine proximity of an object relative to the contact lens. In some aspects, the object can include, but is not limited to, a finger or eyelid.

The material component 310 can receive the sensed capacitance. Based on the change between the baseline capacitance and the sensed capacitance, the material component 310 can determine a type, amount and/or composition of a material on or near the contact lens. For example, the material component 310 can determine a composition of tear fluid incident on the contact lens.

The response component 312 can perform one or more actions on the contact lens. For example, storage or transmission of information sensed can be performed. The one or more actions can be performed based on the sensed capacitance (or parameters and/or conditions determined based on the sensed capacitance). In some aspects, the one or more actions can be performed based on information received from a source external to the contact lens. For example, the communication component 304 can communicate sensed capacitance. An information source external to the contact lens can receive the sensed capacitance and transmit, to the contact lens, information for performing the action by the response component 312.

The power component 316 can generate power for the circuit 206' and/or capacitive sensor coupled to the circuit 206'. In some aspects, the power component 316 can serve as an energy reservoir that outputs current to the capacitive sensor. In various aspects, the power component can generate and/or output electrical and/or RF power.

The memory 318 can be a computer-readable storage medium storing computer-executable instructions and/or information for performing the functions described in this disclosure with reference to the circuit 206'. In some aspects, the memory 318 can store information including, but not limited to, sensed capacitance information, frequency, current, parameters and/or conditions related to the eyelid and/or sensed capacitance.

The logic circuitry 320 can perform one or more of the functions described in this disclosure with reference to the circuit 206' (or components thereof).

FIGS. 5, 6, 7, 8, 9 and 10 are illustrations of exemplary flow diagrams of methods that facilitate capacitive sensing on a contact lens in accordance with aspects described herein.

Figure 5:
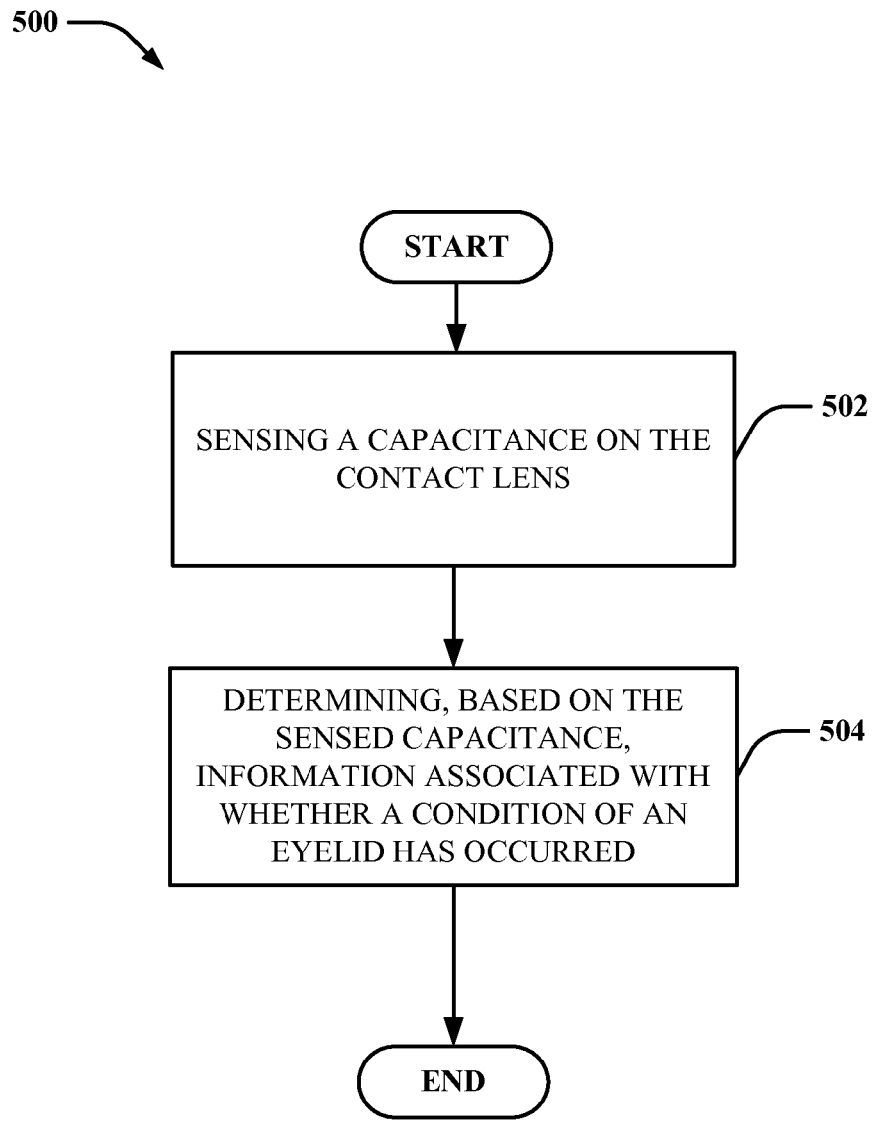
FIGS. 5, 6, 7, 8, 9 and 10 are illustrations of exemplary flow diagrams of methods that facilitate capacitive sensing on a contact lens in accordance with aspects described herein.

Turning first to FIG. 5, at 502, method 500 can include sensing a capacitance on the contact lens (e.g., using the capacitive sensor 204). At 504, method 500 can include determining, based on the sensed capacitance, information associated with whether a condition of an eyelid has occurred (e.g., using the circuit 206, 206'). In some aspects, the condition can be whether or not a blink of the eyelid has occurred, whether the eyelid is closed or open or the like.

As described above, pairs of electrodes can be provided on the contact lens. For example, a first pair can be provided near a top of the contact lens near the eyelid (when the eyelid is in an open position), and a second pair can be provided near the bottom of the contact lens. The bottom can be opposite the top portion of the contact lens. Depending on whether one or both pairs are covered by an eyelid, one or both baseline capacitances will change. As such, a determination can be made as to whether a blink has occurred and/or whether the eyelid is open or closed.

Figure 6:
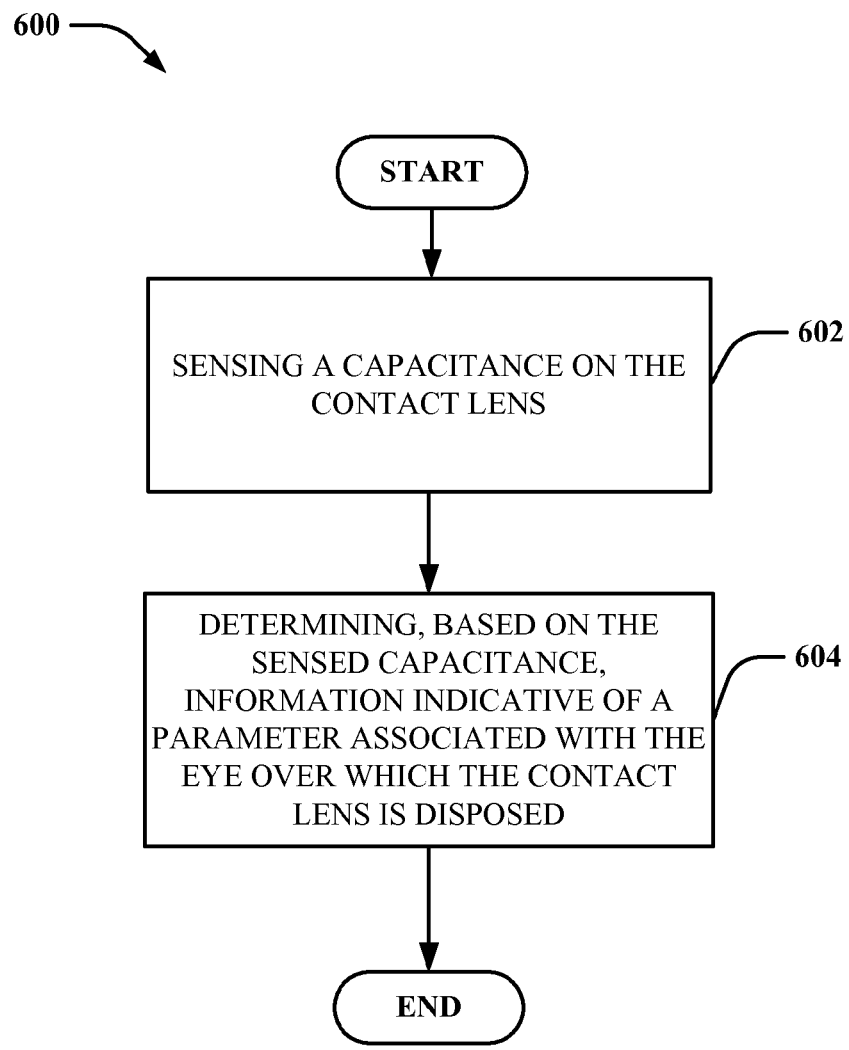

Turning now to FIG. 6, at 602, method 600 can include sensing a capacitance on the contact lens (e.g., using the capacitive sensor 204). At 604, method 600 can include determining, based on the sensed capacitance, information indicative of a parameter associated with the eye over which the contact lens is disposed (e.g., using the circuit 206, 206'). In some aspects, the parameter can include, but is not limited to, a thickness of a layer of material disposed on or within the contact lens, a type of material on or within the contact lens and/or a composition of material on or within the contact lens.

Figure 7:
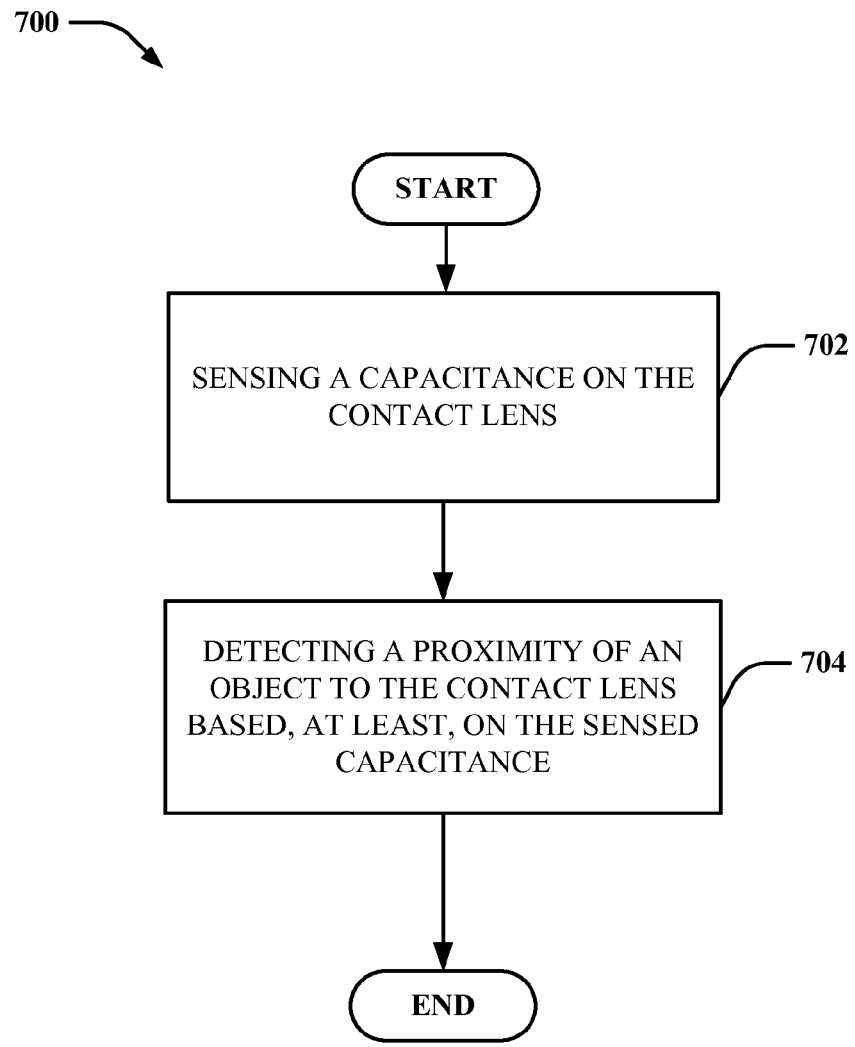

Turning now to FIG. 7, at 702, method 700 can include sensing a capacitance on the contact lens (e.g., using the capacitive sensor 204). At 704, method 700 can include detecting the proximity of an object to the contact lens based, at least, on the sensed capacitance (e.g., using the proximity component 308). For example, the proximity of a finger or eyelid to the contact lens can be detected. As described, the baseline capacitance of the capacitive proximity sensor can change upon sensing the object in a certain proximity to the sensor.

Figure 8:
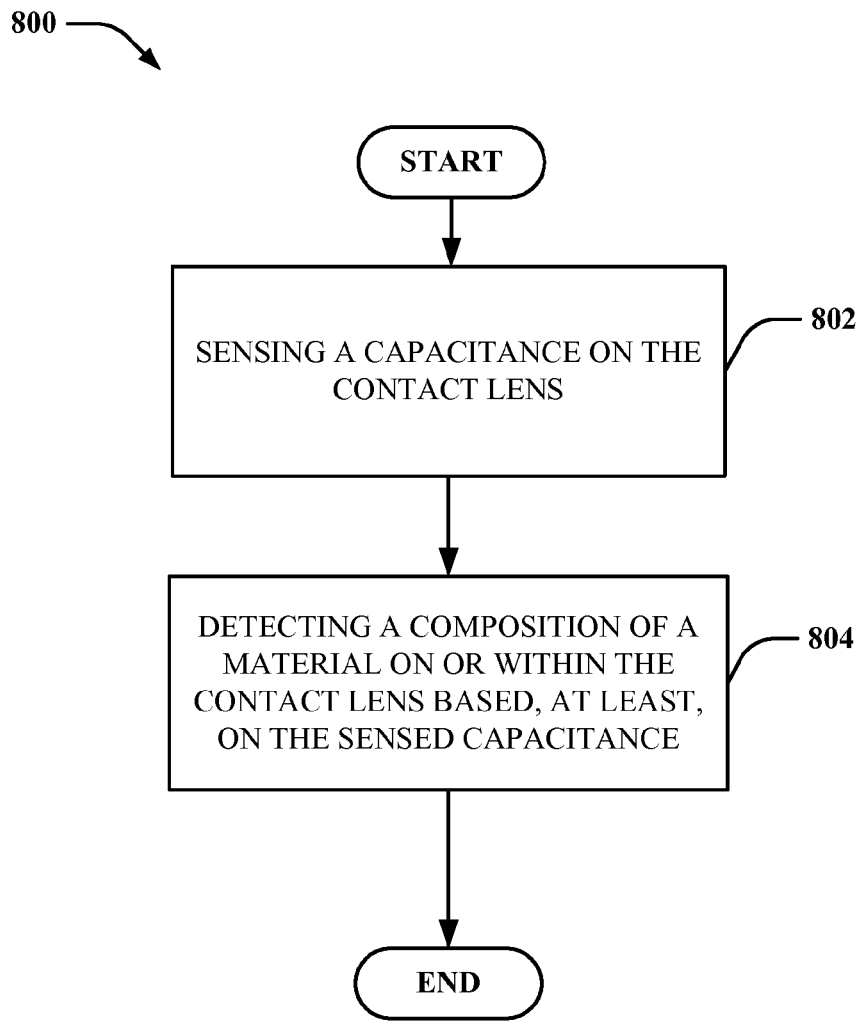

Turning now to FIG. 8, at 802, method 800 can include sensing a capacitance on the contact lens (e.g., using the capacitive sensor 204). At 804, method 800 can include detecting a composition of a material on the contact lens based, at least, on the sensed capacitance (e.g., using the material component 310). In some aspects, for example, the material can be a tear and the composition of one or more chemicals (e.g., glucose, urea, lactate, cholesterol) in the tear can be detected.

Figure 9:
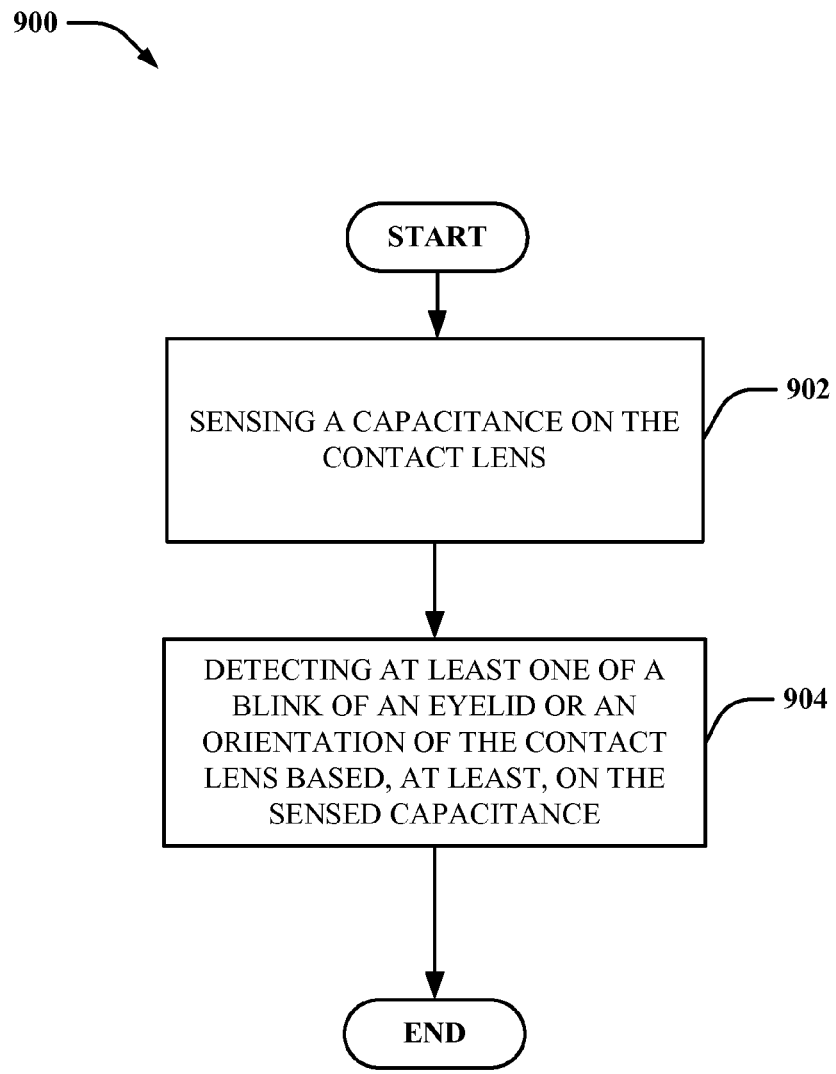

Turning now to FIG. 9, at 902, method 900 can include sensing a capacitance on the contact lens (e.g., using the capacitive sensor 204). At 904, method 900 can include detecting an orientation of the contact lens based, at least, on the sensed capacitance (e.g., using the capacitive analysis component 306).

For example, multiple sensors can be placed on the contact lens. Depending on which sensors are covered during a blink of an eyelid, the orientation of the contact lens can be determined. For example, if sensor A is indicated to be placed at the top of the contact lens and sensor B is indicated to be placed at the bottom, but a change in capacitance is sensed for sensor A at regular intervals (e.g., intervals corresponding to blinks), a determination can be made that sensor A is being covered only at regular intervals as opposed to being continuously covered by being at the top of the contact lens (and hence under the eyelid). In this aspect, a determination can then be made that the contact lens orientation is reversed and the top of the contact lens is actually being worn at the bottom region of the eye.

Figure 10:
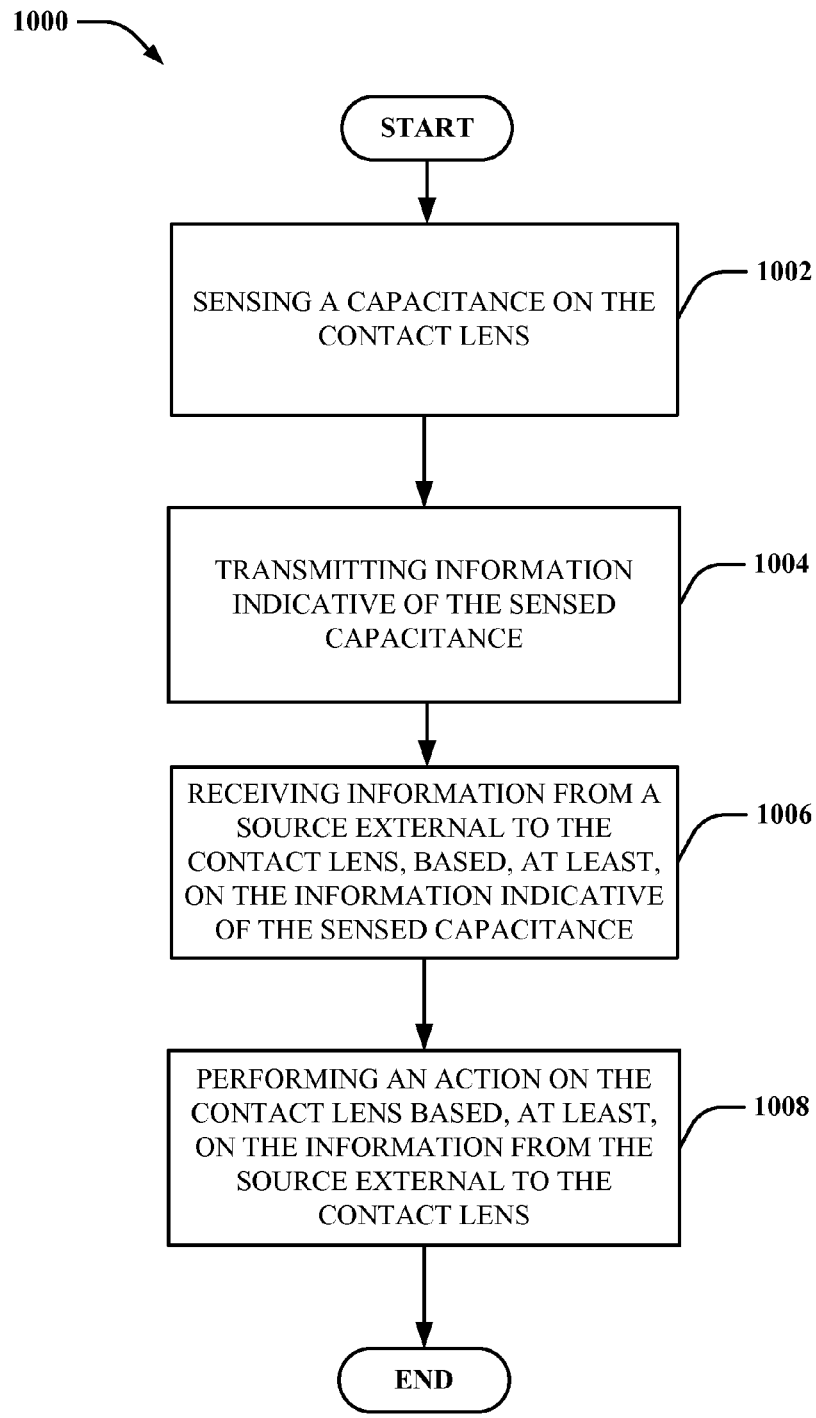

Turning now to FIG. 10, at 1002, method 1000 can include sensing a capacitance on the contact lens (e.g., using the capacitive sensor 204). A condition of the eyelid (e.g., whether the eyelid has blinked, is open, is closed) or a condition of the eye (e.g., whether there is a predetermined fluid level near the eye, whether a particular material or object is within a particular proximity of the eye, a thickness or identity of a material near the eye) can be determined or inferred based on the sensed capacitance.

At 1004, method 1000 can include transmitting information indicative of the sensed capacitance (e.g., using the communication component 304). For example, the information can be transmitted to a reader (e.g., reader 112). In some embodiments, the information can be transferred when the contact lens is within a particular geographic proximity to the reader. Within this geographic proximity, the reader can identify the presence of the contact lens and receive information from the contact lens.

At 1006, method 1000 can include receiving information from a source external to the contact lens based, at least, on the information indicative of the sensed capacitance (e.g., using the communication component 304). For example, the source can be information source 114, which can be remote from the contact lens but communicatively coupled to the contact lens. In some embodiments, the information source 114 can be a repository of instructions or parameters able to read by the circuit of the contact lens to alter the operations of the contact lens.

At 1008, method 1000 can include performing an action on the contact lens based, at least, on the information from the source external to the contact lens (e.g., using the response component 312). In some aspects, the action performed can include storing or reporting the sensed capacitance, and/or storing or reporting parameters and/or information determined based on the sensed capacitance or received from the source external to the contact lens.

Exemplary Networked and Distributed Environments

Figure 11:
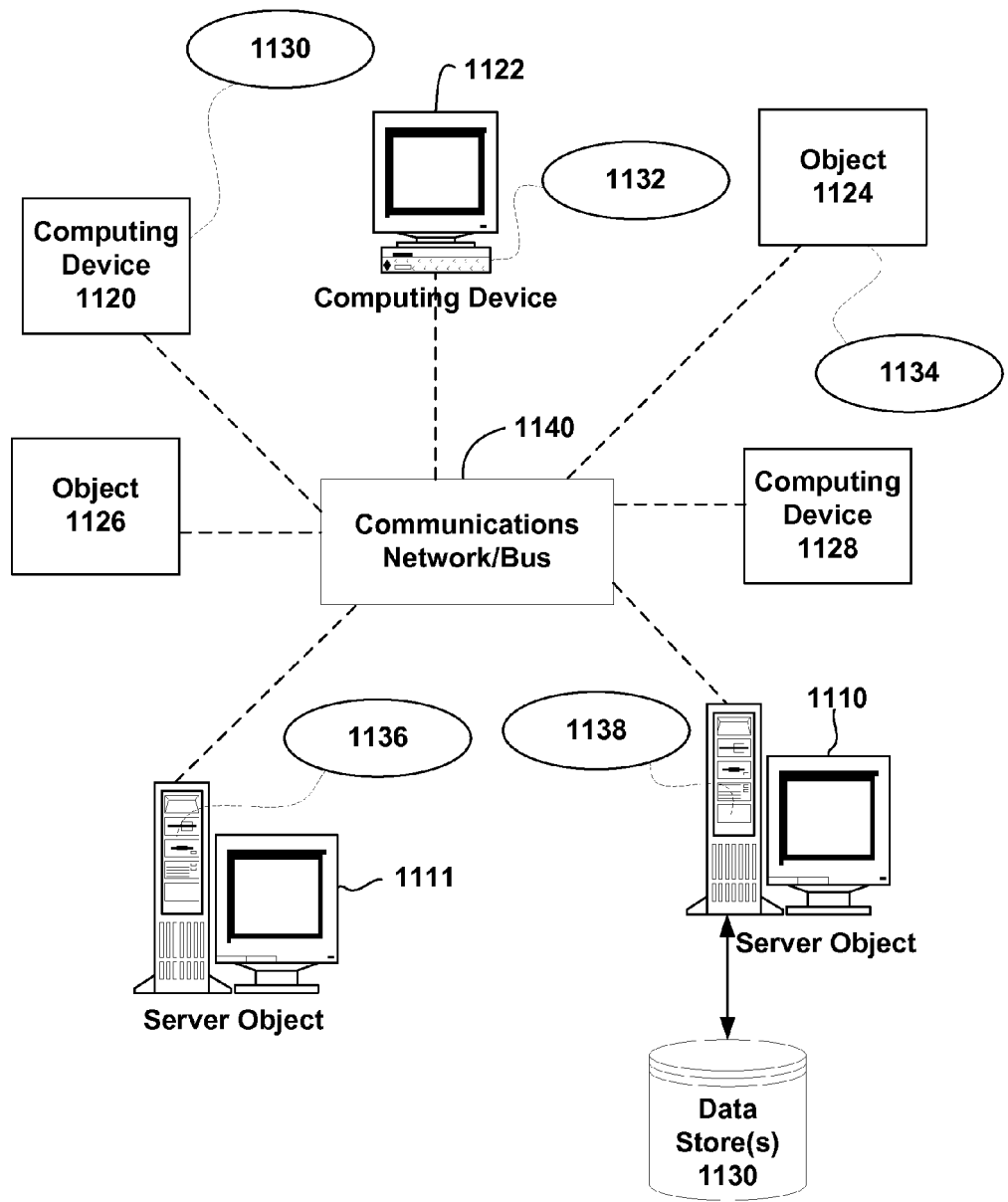
FIG. 11 is an illustration of a schematic diagram of an exemplary networked or distributed computing environment with which one or more aspects described herein can be associated.

FIG. 11 provides a schematic diagram of an exemplary networked or distributed computing environment with which one or more aspects described in this disclosure can be associated. The distributed computing environment includes computing objects 1110, 1112, etc. and computing objects or devices 1120, 1122, 1124, 1126, 1128, etc., which can include programs, methods, data stores, programmable logic, etc., as represented by applications 1130, 1132, 1134, 1136, 1138. It can be appreciated that computing objects 1110, 1112, etc. and computing objects or devices 1120, 1122, 1124, 1126, 1128, etc. can include different devices, such as active contact lenses (and components thereof), personal digital assistants (PDAs), audio/video devices, mobile phones, MPEG-1 Audio Layer 3 (MP3) players, personal computers, laptops, tablets, etc.

Each computing object 1110, 1112, etc. and computing objects or devices 1120, 1122, 1124, 1126, 1128, etc. can communicate with one or more other computing objects 1110, 1112, etc. and computing objects or devices 1120, 1122, 1124, 1126, 1128, etc. by way of the communications network 1140, either directly or indirectly. Even though illustrated as a single element in FIG. 11, network 1140 can include other computing objects and computing devices that provide services to the system of FIG. 11, and/or can represent multiple interconnected networks, which are not shown.

In a network environment in which the communications network/bus 1140 can be the Internet, the computing objects 1110, 1112, etc. can be Web servers, file servers, media servers, etc. with which the client computing objects or devices 1120, 1122, 1124, 1126, 1128, etc. communicate via any of a number of known protocols, such as the hypertext transfer protocol (HTTP).

Exemplary Computing Device

As mentioned, advantageously, the techniques described in this disclosure can be associated with any suitable device. It is to be understood, therefore, that handheld, portable and other computing devices (including active contact lens having circuitry or components that compute and/or perform various functions). As described, in some aspects, the device can be the contact lens (or components of the contact lens) and/or reader described herein. In various aspects, the data store can include or be included within, any of the memory described herein, any of the contact lenses described herein and/or the RF reader described herein. In various aspects, the data store can be any repository for storing information transmitted to or received from the contact lens.

Figure 12:
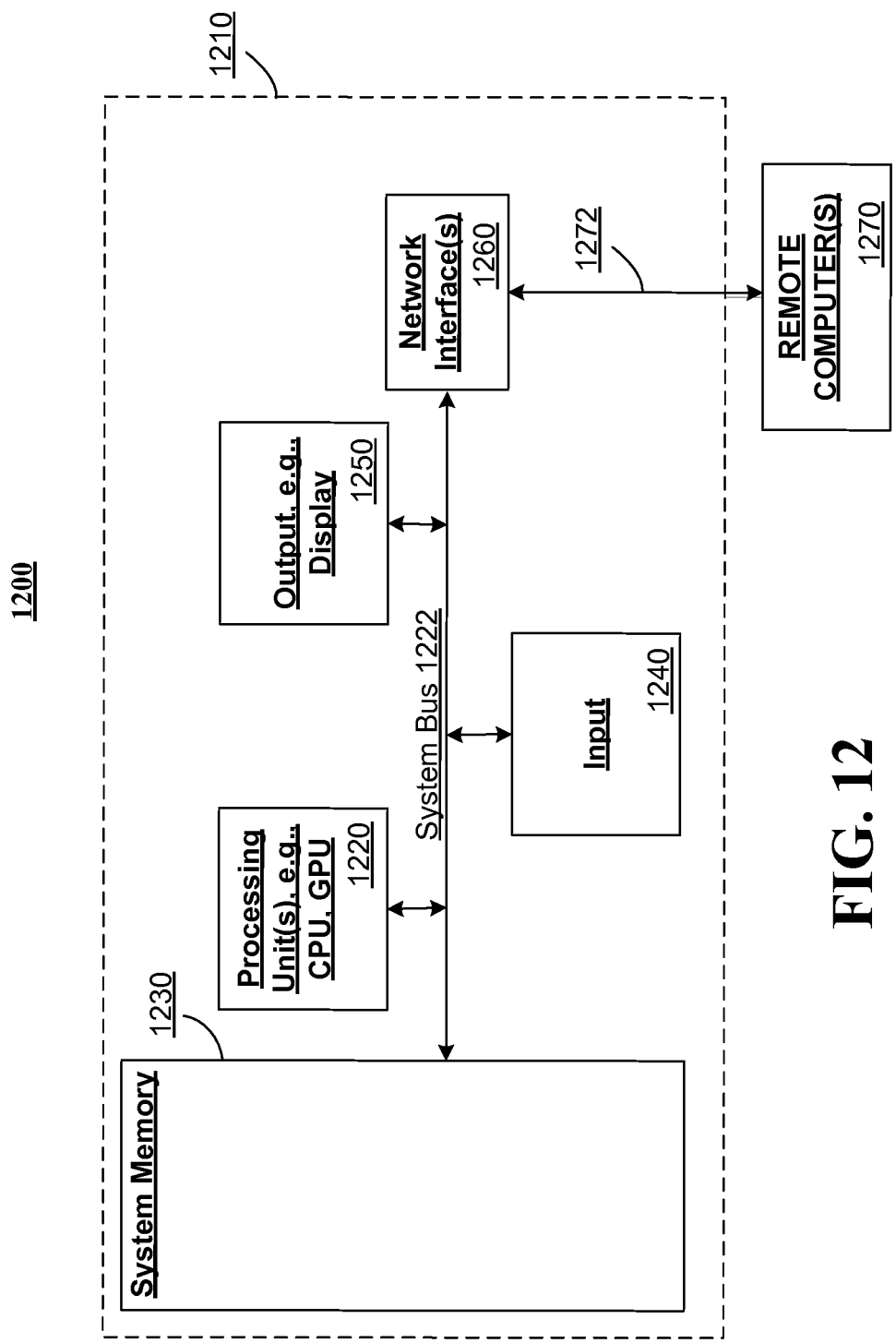
FIG. 12 is an illustration of a schematic diagram of an exemplary computing environment with which one or more aspects described herein can be associated.

FIG. 12 illustrates an example of a suitable computing system environment 1200 in which one or aspects of the aspects described in this disclosure can be implemented. Components of computer 1210 can include, but are not limited to, a processing unit 1220, a system memory 1230, and a system bus 1222 that couples various system components including the system memory to the processing unit 1220.

Computer 1210 typically includes a variety of computer readable media and can be any available media that can be accessed by computer 1210. The system memory 1230 can include computer storage media in the form of volatile and/or nonvolatile memory such as read only memory (ROM) and/or random access memory (RAM). By way of example, and not limitation, memory 1230 can also include an operating system, application programs, other program components, and program data.

A user can enter commands and information into the computer 1210 through input devices 1240 (e.g., keyboard, keypad, a pointing device, a mouse, stylus, touchpad, touch screen, motion detector, camera, microphone or any other device that allows the user to interact with the computer 1210). A monitor or other type of display device can be also connected to the system bus 1222 via an interface, such as output interface 1250. In addition to a monitor, computers can also include other peripheral output devices such as speakers and a printer, which can be connected through output interface 1250.

The computer 1210 can operate in a networked or distributed environment using logical connections to one or more other remote computers, such as remote computer 1280. The remote computer 1280 can be a personal computer, a server, a router, a network PC, a peer device or other common network node, or any other remote media consumption or transmission device, and can include any or all of the elements described above relative to the computer 1210. The logical connections depicted in FIG. 12 include a network 1282, such local area network (LAN) or a wide area network (WAN), but can also include other networks/buses e.g., cellular networks.

Computing devices typically include a variety of media, which can include computer-readable storage media and/or communications media, in which these two terms are used herein differently from one another as follows. Computer-readable storage media can be any available storage media that can be accessed by the computer, can be typically of a non-transitory nature, and can include both volatile and non-volatile media, removable and non-removable media. By way of example, and not limitation, computer-readable storage media can be implemented in connection with any method or technology for storage of information such as computer-readable instructions, program components, structured data, or unstructured data. Computer-readable storage media can include, but are not limited to, RAM, ROM, electrically erasable programmable read only memory (EEPROM), flash memory or other memory technology, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium. In various aspects, the computer-readable storage media can be, or be included within, the memory, contact lens (or components thereof) or reader described herein.

On the other hand, communications media typically embody computer-readable instructions, data structures, program components or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals.

It is to be understood that the aspects described in this disclosure can be implemented in hardware, software, firmware, middleware, microcode, or any combination thereof. For a hardware aspect, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors and/or other electronic units designed to perform the functions described in this disclosure, or a combination thereof.

For a software aspect, the techniques described in this disclosure can be implemented with components or components (e.g., procedures, functions, and so on) that perform the functions described in this disclosure. The software codes can be stored in memory units and executed by processors.

What has been described above includes examples of one or more aspects. It is, of course, not possible to describe every conceivable combination of components or methodologies for purposes of describing the aforementioned aspects, but one of ordinary skill in the art can recognize that many further combinations and permutations of various aspects are possible. Accordingly, the described aspects are intended to embrace all such alterations, modifications and variations that fall within the spirit and scope of the appended claims.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

The aforementioned systems have been described with respect to interaction between several components. It can be appreciated that such systems and components can include those components or specified sub-components. Sub-components can also be implemented as components communicatively coupled to other components rather than included within parent components (hierarchical). Additionally, it is to be noted that one or more components can be combined into a single component providing aggregate functionality. Any components described in this disclosure can also interact with one or more other components not specifically described in this disclosure but generally known by those of skill in the art.

In view of the exemplary systems described above methodologies that can be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks can occur in different orders and/or concurrently with other blocks from what is depicted and described in this disclosure. Where non-sequential, or branched, flow is illustrated via flowchart, it can be appreciated that various other branches, flow paths, and orders of the blocks, can be implemented which achieve the same or a similar result. Moreover, not all illustrated blocks may be required to implement the methodologies described in this disclosure after.

In addition to the various aspects described in this disclosure, it is to be understood that other similar aspects can be used or modifications and additions can be made to the described aspect(s) for performing the same or equivalent function of the corresponding aspect(s) without deviating there from. Still further, multiple processing chips or multiple devices can share the performance of one or more functions described in this disclosure, and similarly, storage can be provided across a plurality of devices. The invention is not to be limited to any single aspect, but rather can be construed in breadth, spirit and scope in accordance with the appended claims.

What is claimed is:

1. An apparatus, comprising:
  a contact lens, comprising:
    a substrate;
    a capacitive sensor, disposed on or within the substrate, that senses capacitance on the contact lens; and
    a circuit disposed on or within the substrate that determines information indicative of the capacitance from the capacitive sensor and comprising a capacitance analysis component that determines an amount of pressure applied by an object in proximity to the contact lens based on the sensed capacitance.

2. The apparatus of claim 1, wherein the capacitive sensor is a capacitive proximity sensor.

3. The apparatus of claim 1, wherein the capacitive sensor is a capacitive pressure sensor.

4. The apparatus of claim 1, wherein the circuit comprises a communication component that:
   transmits the information to a reader.

5. The apparatus of claim 1, wherein the circuit further comprises a capacitance analysis component that determines a condition of an eyelid associated with an eye over which the contact lens is disposed.

6. The apparatus of claim 5, wherein the condition comprises a blink of the eyelid.

7. The apparatus of claim 5, wherein the condition comprises an orientation of the contact lens.

8. The apparatus of claim 1, further comprising a reader that receives information transmitted from the contact lens.

9. The apparatus of claim 8, wherein the circuit further comprises a communication component that at least one of: transmits the information to the reader or receives information from a source external to the contact lens.

10. The apparatus of claim 1, wherein the circuit further comprises a processing component that performs an action on the contact lens based, at least, on the information indicative of the capacitance.

11. A method, comprising:
   using a sensor on a contact lens to detect capacitance;
   determining change in the capacitance;
   determining or inferring a change in condition of an eye based on the change in the capacitance; and
   determining, based on the detected capacitance, an amount of pressure applied by an object in proximity to the contact lens.

12. The method of claim 11, wherein the capacitance is detected in response to proximity of an object to the contact lens.

13. The method of claim 11, wherein the capacitance is detected in response to at least one of a presence of a material sensed on the contact lens, or pressure on the contact lens.

14. The method of claim 11, further comprising determining, based on the detected capacitance, at least one of a thickness of a layer of material disposed on or within the contact lens, type of material on the contact lens or composition of material on the contact lens.

\* \* \* \* \*